United States Patent [19]

Kato et al.

[11] Patent Number: 4,487,714

[45] Date of Patent: Dec. 11, 1984

[54] CYTOCIDAL MODIFIED IMMUNOGLOBULIN AND PROCESS FOR THE PREPARATION THEREOF

[75] Inventors: Yoshinori Kato; Naoji Umemoto, both of Hino; Yumiko Takeda, Higashimurayama; Takeshi Hara, Hachioji, all of Japan

[73] Assignee: Teijin Limited, Osaka, Japan

[21] Appl. No.: 571,898

[22] Filed: Jan. 18, 1984

[30] Foreign Application Priority Data

Jan. 19, 1983 [JP] Japan ................... 58-5807

[51] Int. Cl.³ ................... C07G 7/00; C07C 103/52; A61K 39/44; A61K 39/395
[52] U.S. Cl. ................... 260/112 B; 424/85
[58] Field of Search ................... 260/112 B; 424/85

[56] References Cited

U.S. PATENT DOCUMENTS

| | | | |
|---|---|---|---|
| 4,046,722 | 9/1977 | Rowland | 260/112 B X |
| 4,093,607 | 6/1978 | Sela et al. | 260/112 B |
| 4,315,851 | 2/1982 | Yoshikumi et al. | 260/112 B |
| 4,401,592 | 8/1983 | Yoshikumi et al. | 260/112 B |

*Primary Examiner*—Howard E. Schain
*Attorney, Agent, or Firm*—Sughrue, Mion, Zinn, Macpeak, and Seas

[57] ABSTRACT

A cytocidal modified immunoglobulin expressed by formula (I)

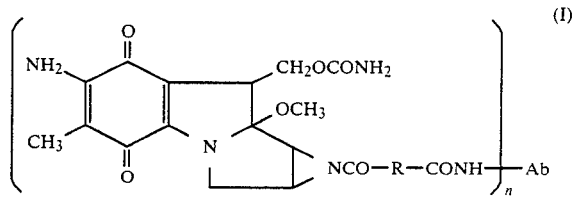

(wherein Ab represents an immunoglobulin or its fragment; R represents a divalent organic group; and n is an integer from 1 to 20).

4 Claims, 3 Drawing Figures

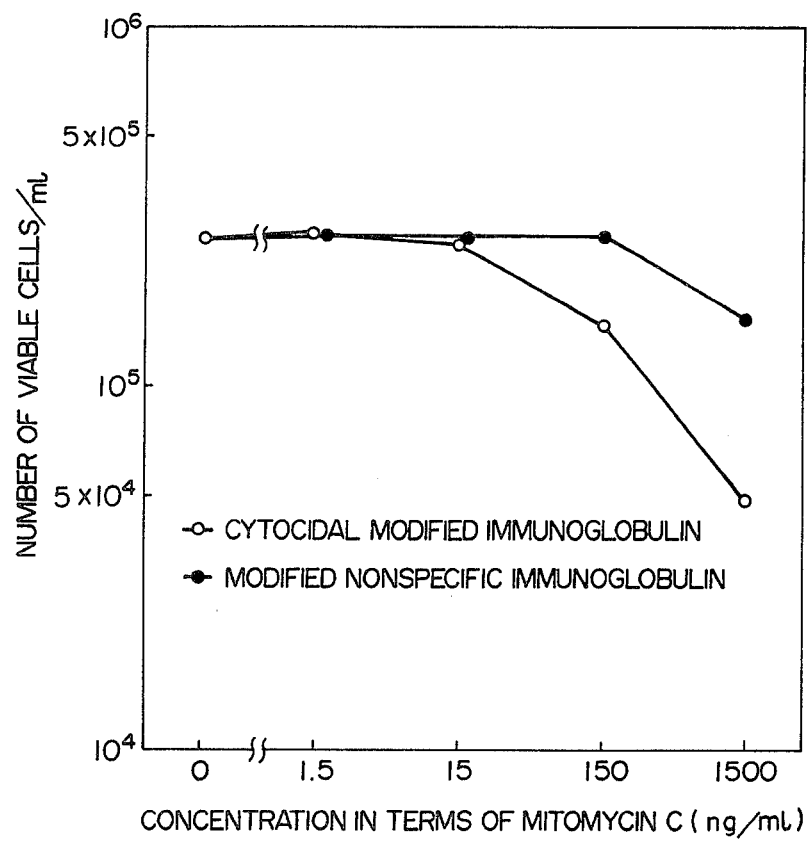

CYTOCIDAL MODIFIED IMMUNOGLOBULIN AND PROCESS FOR THE PREPARATION THEREOF

BACKGROUND OF THE INVENTION

1. Field of the Invention

The present invention relates to a novel cytocidal modified immunoglobulin and a process for the preparation thereof, and more particularly relates to a novel cytocidal modified immunoglobulin comprising an immunoglobulin, which is capable of selectively binding to a particular antigen possessed by a cell to be killed (hereinafter referred to as a target cell), or its fragment having an antigen-binding moiety, whose amino group is linked with a mitomycin C derivative and a process for the preparation thereof.

2. Description of the Prior Art

It is a publicly known art to have the carboxyl group of an antibody linked with mitomycin C by allowing a large quantity of mitomycin C to contact with an antibody protein in the presence of water-soluble carbodiimide (Japanese Patent Application Laid-open No. 92325/80).

In this publicly known method in which a condensing agent of 1-ethyl-3-(3-dimethylaminopropyl)carbodiimide is used as a means for forming the amide linkage between the amino group and the carboxyl group, undesirable phenomena such as an intramolecular reaction between the amino group and carboxyl group in the molecule of an antibody protein and an intermolecular reaction between such groups of the antibody molecules take place, thus causing a considerable loss of the antigen-recognizing activity of the antibody or the formation of macromolecular aggregates whose presence in the drugs is undesirable.

To minimize such undesirable phenomena, mitomycin C which constitutes the amino component to be used in the abovementioned method must necessarily be used in a large excess in the reaction. This is not an advantageous mode of production from the industrial viewpoint.

There is another publicly known method of obtaining a conjugate of an antibody and mitomycin C by treating the antibody protein with cyanogen bromide, followed by the treatment with a large quantity of mitomycin C (Japanese Patent Application Laid-open No. 135421/51). However, this procress can hardly be said to be useful from the industrial viewpoint because in the conjugate obtained according to this method, only one molecule of mitomycin C is linked with the antibody protein molecule.

SUMMARY OF THE INVENTION

As a result of extensive study, the inventors of the present invention have come to find that a modified immunoglobulin obtained by making a mitomycin C derivative, which contains an active ester group in its structure, react with an immunoglobulin to have its amino group linked with said active ester group, has an excellent selective cytocidal property and that this is a modified immunoglobulin which can be prepared very advantageously on an industrial scale, thus completing this invention.

The present invention is directed to a cytocidal modified immunoglobulin expressed by the following formula (I)

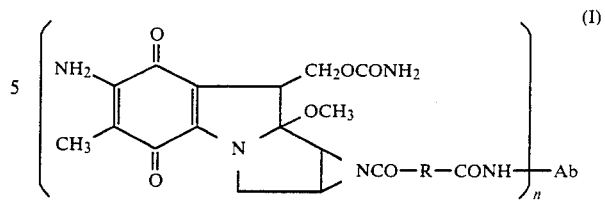

(wherein
Ab represents an immunoglobulin or its fragment;
R represents a divalent organic group; and
n is an integer from 1 to 20,)
and a process for the preparation thereof comprising allowing a mitomycin C derivative expressed by the following formula (II) to react with an immunoglobulin or its fragment

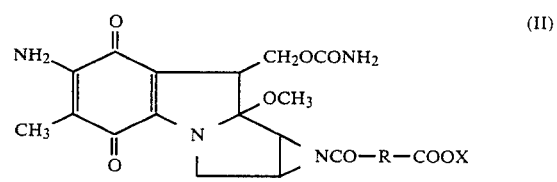

(wherein
R represents a divalent organic group and
X represents a residue arising from the alcohol moiety of the active ester).

BRIEF DESCRIPTION OF THE DRAWINGS

FIGS. 1 to 3 show how effectively the cytocidal modified immunoglobulin of the present invention functions in inhibiting the proliferation of mouse mammary carcinoma MM46 cells.

DESCRIPTION OF THE PREFERRED EMBODIMENT

Figure 1:
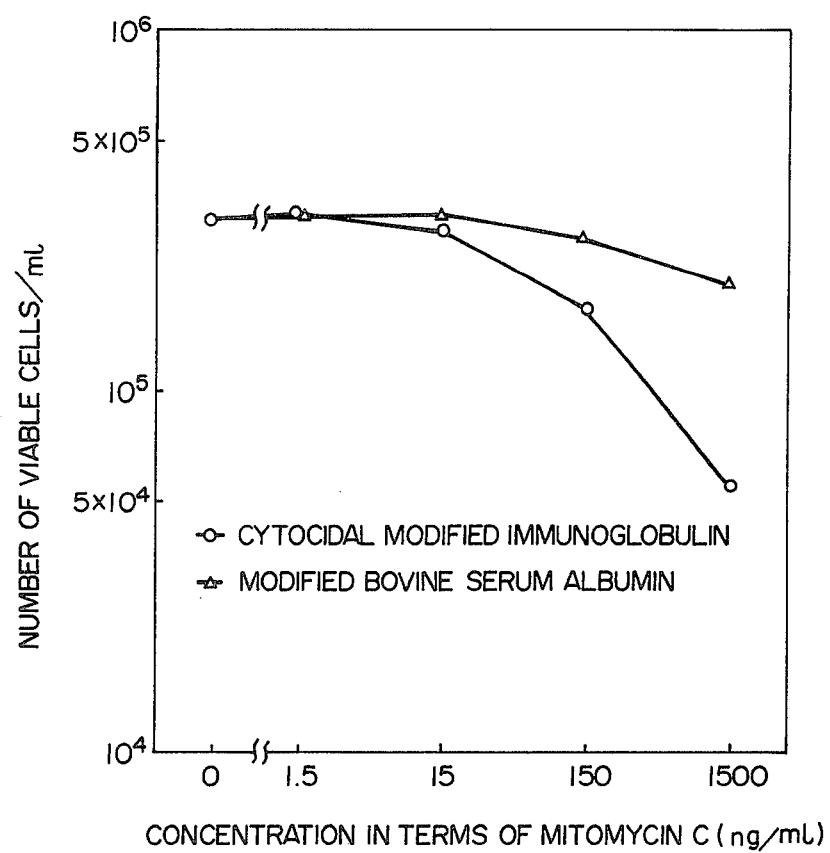

In the abovementioned formulas (I) and (II), $R^2$ represents a divalent organic group and alkylene groups having 2 to 7 carbon atoms such as ethylene group, trimethylene group, tetramethylene group, pentamethylene group, 2-methyltrimethylene group, etc. may be mentioned as desirable ones and especially desirable one is the trimethylene group. As the alcohol rest of an active ester expressed by X in the formula (II), succinimidyl group, 5-norbornane-2,3-dicarboxyimidyl group, phthalimidyl group, p-nitrophenyl group, 2,4-dinitrophenyl group, 2,4,5-trichlorophenyl group, pentachlorophenyl group, etc. may be mentioned.

What is referred to as an immunoglobulin in the present invention means an immunoglobulin which is capable of binding to a particular antigen possessed by a cell to be killed. And such immunoglobulin to be used in the present invention is a globulin (antibody) which can be obtained, for instance, from the antiserum taken from man or such animals as monkey, horse, ox, goat, sheep, rabbit, guinea pig, hamster, rat, mouse, etc. that are immunized with tumor cells, or target cells such as certain lymphocytes, or tissue containing such cells, by any of publicly known methods including ethanol fractionation, ammonium sulfate fractionation, ion exchange, molecular sieve column chromatography, etc.; or from a culture solution of cells obtained by the cancerization of antibody-producing cells which are collected from an animal immunized with the target cells, with a cancer-causing virus, or a culture solution of the desired antibody-producing clone selected from the hybridoma obtained by hybridizing an antibody-producing cell with a myeloma cell, etc., or from the serum or ascitic fluid of an animal innoculated with such hybridoma. The immunoglobulin comes under five categories, i.e. IgG, IgA, IgM, IgD, and IgE, and all of them are applicable to the present invention.

In the present invention, both the immunoglobulin itself and its fragment (i.e., Fab, Fab', F(ab')$_2$ or a dimer of Fab'), so far as the fragment contains a moiety which is capable of binding to an antigen, can be used.

Since an immunoglobulin or its fragment has in its molecule plural terminal amino groups or amino groups arising from lysine, a constitutive amino acid, these amino groups are advantageously utilized in the preparation of the cytocidal modified immunoglobulin of the present invention. The number of utilizable amino groups should desirably be in the range of 1 to 20. The cytocidal modified immunoglobulin expressed by formula (I) of this invention is prepared by making a mitomycin C derivative expressed by formula (II) react with an immunoglobulin or its fragment. This reaction is carried out by adding a mitomycin C derivative of formula (II), which is dissolved in a small amount of a solvent such as N,N-dimethylformamide, methanol, ethanol, and acetone, to a buffer solution (pH 5~8) of immunoglobulin or its fragment (protein concentration preferably adjusted to 0.5~100 mg/ml), desirably at a ratio of 1~50 moles of the mitomycin C derivative to 1 mole of the immunoglobulin or its fragment, at 0° to 40° C. with stirring, and by allowing the mixture to react for 15 minutes to 12 hours. Thereafter, the reaction product is subjected to gel filtration or dialysis to remove the unreacted mitomycin C derivative and low-molecular-weight reaction product and purify the obtained cytocidal modified immunoglobulin.

The mitomycin C derivative expressed by formula (II) to be used in the present invention can be prepared from the starting materials mitomycin C and acid anhydride of dibasic carboxylic acid processed in accordance with the route mentioned below. As the desirable acid anhydride to be used, succinic anhydrice, glutaric anhydride, 3-methylglutaric anhydride, etc. may be mentioned.

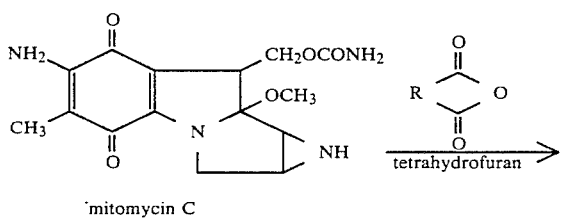

mitomycin C

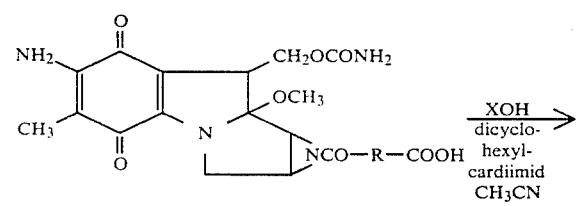

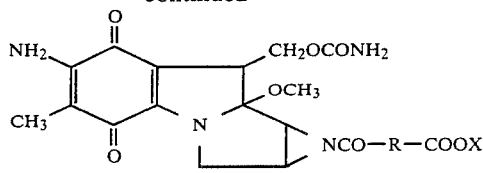

[II]

As the alcohol residue of active ester, there are, for instance,

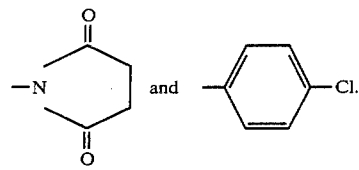

The cytocidal modified immunoglobulin obtained in the present invention has a selective cytotoxic activity against the target cells.

The following examples and referential examples are presented to further illustrate the present invention.

REFERENTIAL EXAMPLE

Preparation of rabbit anti-L1210 immunoglobulin:

An emulsion prepared from $10^6$ of mouse leukemia L1210 cells and Freund's complete adjuvant was intravenously injected to rabbits. Thereafter, about $10^6$ of L1210 cells, together with the adjuvant, were subcutaneously injected to the rabbits three times at one-week intervals and the rabbits were bled 8 days after the day of final injection. The obtained blood was pooled and serum was separated from the mixed blood. The serum was then inactivated at 56° C. for 30 minutes. 200 ml of a saturated aqueous solution of ammonium sulfate was added to 200 ml of thus obtained anti-L1210 antiserum and the formed precipitate was separated by centrifugation. The obtained precipitate was dissolved in 50 ml of 0.1M phosphate buffer (pH 7.6) and dialyzed thoroughly against the same buffer. The dialyzate was subjected to diethylamonoethyl cellulose column chromatography (column size 3 cm×94 cm) equilibrated with the same buffer to obtain a solution containing the desired rabbit anti-L1210 IgG antibody as an unadsorbed fraction.

REFERENTIAL EXAMPLE 2

Preparation of mouse monoclonal anti-MM46 immunoglobulin:

A hybridoma secreting mouse monoclonal antibody IgG2b against mouse mammary carcinoma MM46 cells (see Seto et al., Journal of Immunology, vol. 128, page 201, 1982) was implanted to BALB/c nude mice and their ascitic fluid was obtained 10 days thereafter.

After 4 ml of thus obtained ascitic fluid was dialyzed against 0.1M phosphate buffer (pH 8.0), the dialyzate was passed through a column (1.5 cm×22 cm) of Protein A Sepharose CL-4B equilibrated with the same buffer. The column was washed thoroughly with the same buffer, eluted with 0.1M citrate buffer (pH 4.5) to remove nonspecific immunoglobulin, and then with 0.1M citrate buffer (pH 3.5) to give the desired mouse monoclonal anti-MM46 antibody IgG2b (10 mg). The eluted antibody was made to precipitate by 50% saturation with ammonium sulfate. The precipitate was again dissolved in a small quantity of 0.9% sodium chloride solution and was dialyzed thoroughly against 0.1M phosphate buffer (pH 7.5) containing 0.1M sodium chloride (hereinafter called buffer A).

EXAMPLE 1

IgG2b +

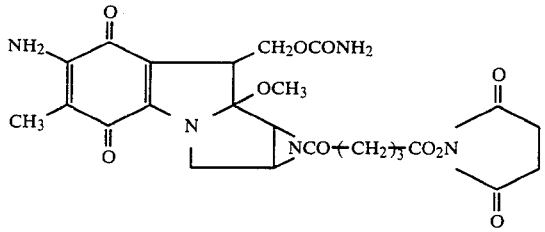

1a-[4-(N—Succinimidoxycarbonyl)-butyryl]mitomycin C ⟶

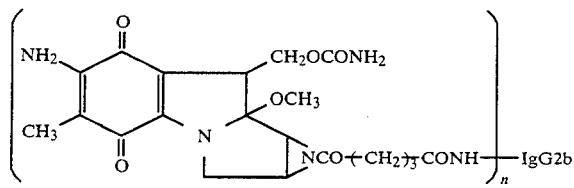

(a) Preparation of cytocidal modified immunoglobulin:

0.1 ml of dimethylformamide containing 0.71 mg of 1a-[4-(N-succinimidoxycarbonyl)butyryl]mitomycin C dissolved therein was added to 5.1 ml of buffer A containing 9.74 mg of mouse monoclonal anti-MM46 antibody IgG2b dissolved therein prepared in the preceding Referential Example 2 little by little with moderate stirring and thereafter the mixture was allowed to stand at 4° C. for 5 hours to complete the reaction (that is, the reaction was carried out by adding 20 molecules of mitomycin C derivative to 1 molecule of antibody). The reaction solution was subjected to gel filtration on a Sephadex G-25 column (1.0 cm×48 cm) in 0.9 sodium chloride solution to remove the unreacted mitomycin C derivative and low-molecular-weight reaction product, thus giving 4.3 ml of the desired cytocidal modified immunoglobulin solution.

The concentration of mitomycin C residue linked in the cytocidal modified immunoglobulin was determined to be 20.9 μg/ml from the absorbance at 360 nm and the concentration of IgG2b was determined to be 1.30 mg/ml from the quantitation of protein according to the Bio-Rad protein assay (M. Bradford, Analitical Biochemistry, vol. 72, p.248, 1976). From these values, the number of mitomycin C residues linked to one molecule IgG2b antibody is assumed to be 7.7.

(b) Determination of activity of cytocidal modified immunoglobulin to inhibit proliferation of cancerous cells in vitro:

The cytocidal modified immunoglobulin prepared in the preceding (a) was added to mouse mammary carcinoma MM46 cells cultured in vitro at the concentration of 0∼1500 μg/ml in terms of mitomycin C and the culture was continued for 48 hours. The number of viable cells was determined under a microscope by staining the cells with Trypan Blue. A modified bovine serum albumin was separately prepared by modifying a bovine serum albumin, which had no specific affinity for MM46 cells, with 1a-[4-(N-succinimidoxycarbonyl)-butyryl]mitomycin C according to the same method as that in the preceding (a), and this was used as a control. The result of the experiment is shown in FIG. 1.

It is confirmed from FIG. 1 that, though the modified albumin shows an inadequate activity, the modified immunoglobulin of the present invention has a strong activity to inhibit the proliferation of the cells varying in accordance with the concentration of mitomycin C derivative, thus proving that the modified immunoglobulin reacted specifically with the target MM46 cells.

The culture conditions were as follows:

| | |
|---|---|
| The number of cells when the culture started | $2.5 \times 10^4$ cells/ml, 0.2 ml |
| Culture medium | RPMI1640 + 10% fetal calf serum + 20 μM 2-mercaptoethanol |
| Temperature | 37° C. |
| Atmosphere | 5% carbon dioxide |

EXAMPLE 2

(a) 12 μl of 70 mM DMF solution of 1a-[4-(N-succinimidoxycarbonyl)butyryl]mitomycin C was added to 1.0 ml of 0.1M phosphate buffer (pH 7.0) containing 5.3 mg of rabbit IgG obtained in Referential Example 1 while being cooled with ice, and the mixture was allowed to stand at 4° C. overnight to complete the reaction. After the precipitation was separated by centrifugation, the supernatant solution was subjected to gel filtration an Sephadex G-25 column (column size 1 cm×40 cm) in 10 mM phosphate buffer—0.14M sodium chloride, pH 7.0 to collect the fractions of the high-molecular-weight material, thus obtaining the desired rabbit IgG modified with a mitomycin C derivative.

(b) The quantity of mitomycin C residue linked in the modified rabbit IgG obtained in the preceding (a) was determined from its absorption in the ultraviolet as follows. The modified rabbit IgG exhibited its absorption maxima at 280 nm and 360 nm, and the concentration of IgG protein was determined from the absorbance at 280 nm and the concentration of mitomycin C residue was determined from the absorbance at 360 nm. The number of mitomycin C residue contained in one molecule of IgG is obtained as the ratio between the two molar concentration values. It was found that the modified globulin obtained in the preceding (a) had 7.6 mitomycin C residues per IgG molecule.

The modified immunoglobulin obtained in this Example displayed a cytocidal activity against mouse leukemia L1210 cells.

EXAMPLE 3

(a) Determination of activity of cytocidal modified immunoglobulin to inhibit proliferation of cancerous cells in vitro:

The cytocidal modified immunoglobulin prepared in Example 1, (a), was added to mouse mammary carcinoma MM46 cells cultured in vitro at the concentration of 0∼1500 μg/ml in terms of mitomycin C and the culture was continued for 48 hours. The number of viable cells was then determined under a microscope by staining the cells with Trypan Blue. The anti-MM46 immunoblogulin which was not modified with 1a-[4-(N-succinimidoxycarbonyl)butyryl]mitomycin C was used as a control for comparison. The result is shown in FIG. 2.

Figure 2:
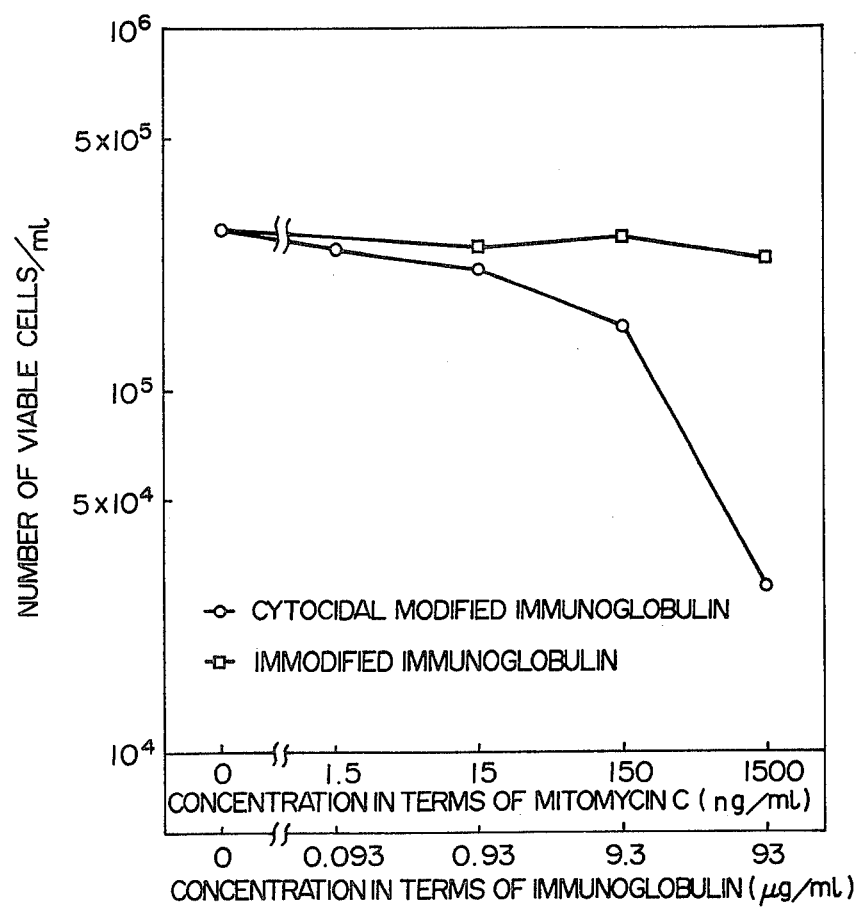

It is confirmed from FIG. 2 that, while the unmodified immunoglobulin shows no cytocidal activity, the cytocidal modified immunoglobulin of the present invention has a strong activity to inhibit the proliferation of the cells varying in accordance with the concentration of the mitomycin C derivative, thus proving that the cytocidal modified immunoglobulin reacted specifically with the target MM46 cells.

The culture conditions were as follows:

| The number of cells when the culture started | $2.5 \times 10^4$ cells/ml, 0.2 ml |
| --- | --- |
| Culture medium | RPMI1640 + 10% fetal calf serum + 20 μM 2-mercaptoethanol |
| Temperature | 37° C. |
| Atmosphere | 5% carbon dioxide |

(b) Determination of activity of cytocidal modified immunoglobulin to inhibit proliferation of cancerous cells in vitro:

The cytocidal modified immunoglobulin prepared in the aforementioned Example 1, (a), was added to mouse mammary carcinoma MM46 cells cultured in vitro at the concentration of 0~1500 μg/ml in terms of mitomycin C, and the culture was continued for 48 hours. The number of viable cells was determined under a microscope by staining the cells with Trypan Blue. Nonspecific immunoglobulin of normal mouse which had no specific affinity for MM46 cells was modified with 1a-[4-(N-succinimidoxycarbonyl)butyryl]mitomycin C according to the same way as the aforementioned Example 1, (a), and was used as a control for comparison. The result is shown in FIG. 3.

FIG. 3 clearly shows that, while the modified nonspecific immunoglobulin displays a very weak activity, the cytocidal modified immunoglobulin of the present invention has a strong activity to inhibit the proliferation of the cells varying in accordance with the concentration of mitomycin C derivative, thus proving that the cytocidal modified immunoglobulin reacted specifically with the target MM46 cells to exert a cytotoxic action on them.

The culture conditions were as follows:

| The number of cells when the culture started | $2.5 \times 10^4$ cells/ml, 0.2 ml |
| --- | --- |
| Culture medium | RPMI1640 + 10% fetal calf serum + 20 μM 2-mercaptoethanol |
| Temperature | 37% |
| Atmosphere | 5% carbon dioxide |

What is claimed is:

1. A cytocidal modified immunoglobulin expressed by formula (I)

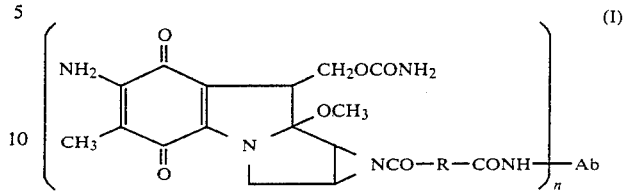

(wherein
Ab represents an immunoglobulin or its fragments;
R represents a divalent organic group; and
n is an integer from 1 to 20).

2. The cytocidal modified immunoglobulin according to claim 1, wherein said R in formula (I) represents an alkylene group having 2 to 7 carbon atoms.

3. The cytocidal modified immunoglobulin according to claim 1 or claim 2, wherein said R in formula (I) represents the trimethylene group.

4. A process for the preparation of a cytocidal modified immunoglobulin expressed by formula (I)

(I)

$$\left( \begin{array}{c} \text{structure with } NH_2, CH_3, O, CH_2OCONH_2, OCH_3, N, NCO-R-CONH \end{array} \right)_n - Ab$$

(wherein
Ab represents an immunoglobulin or its fragment;
R represents a divalent organic group; and
n is an integer from 1 to 20,)
characterised by allowing a mitomycin C derivative expressed by formula (II) to react with an immunoglobulin or its fragment (II)

$$\text{structure with } NH_2, CH_3, O, CH_2OCONH_2, OCH_3, N, NCO-R-COOX$$

(wherein R is as defined with regard to formula (I); and X represents a residue arising from the alcohol moiety of the active ester).

* * * * *